(12) United States Patent
Tata et al.

(10) Patent No.: US 12,357,167 B2
(45) Date of Patent: Jul. 15, 2025

(54) MULTIFUNCTIONAL VISUALIZATION INSTRUMENT WITH ORIENTATION CONTROL

(71) Applicant: Covidien AG, Neuhausen am Rheinfall (CH)

(72) Inventors: Derek Scot Tata, Loveland, CO (US);
Craig Allen Patton, Boulder, CO (US);
Peter Douglas Colin Inglis, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 18/185,815

(22) Filed: Mar. 17, 2023

(65) Prior Publication Data
US 2023/0225605 A1    Jul. 20, 2023

Related U.S. Application Data

(62) Division of application No. 16/802,242, filed on Feb. 26, 2020, now Pat. No. 11,684,251.
(Continued)

(51) Int. Cl.
*A61B 1/267*    (2006.01)
*A61B 1/00*    (2006.01)
(Continued)

(52) U.S. Cl.
CPC .......... *A61B 1/267* (2013.01); *A61B 1/00006* (2013.01); *A61B 1/000094* (2022.02);
(Continued)

(58) Field of Classification Search
CPC ... A61B 1/0005; A61B 1/00052; A61B 1/267; A61B 5/065; A61B 5/066; A61B 5/067;
(Continued)

(56) References Cited

U.S. PATENT DOCUMENTS 9,498,112 B1 * 11/2016 Stewart .................... A61B 1/05
2003/0018235 A1    1/2003 Chen
(Continued)

FOREIGN PATENT DOCUMENTS

WO    WO-2015110929 A1 *    7/2015    ......... A61B 1/00149

OTHER PUBLICATIONS

International Search Report and Written Opinion for PCT/US2020/051734 dated May 14, 2020; 11 pgs.
(Continued)

*Primary Examiner* — Aaron B Fairchild
*Assistant Examiner* — Stephen Floyd London

(57) ABSTRACT

A multifunctional laryngoscope is provided that includes a handle comprising a proximal end and a distal end and a display screen on the handle. The laryngoscope includes a laryngoscope camera at the distal end of the handle and an introducer comprising an orientation sensor at a distal end of the introducer. The laryngoscope includes a processor programmed to execute instructions for receiving from a steering input a steering command in a first reference frame, and mapping the steering command to a second reference frame oriented to the distal end of the introducer based on an orientation signal from the orientation sensor.

20 Claims, 8 Drawing Sheets

Related U.S. Application Data

(60) Provisional application No. 62/812,678, filed on Mar. 1, 2019.

(51) Int. Cl.
*A61B 1/005* (2006.01)
*A61B 1/05* (2006.01)

(52) U.S. Cl.
CPC ........ *A61B 1/00039* (2013.01); *A61B 1/0004* (2022.02); *A61B 1/00045* (2013.01); *A61B 1/0052* (2013.01); *A61B 1/05* (2013.01)

(58) Field of Classification Search
CPC .............. A61B 5/068; A61B 2090/368; A61B 2562/0219; A61B 1/00097; A61B 1/0004; A61B 1/00042; A61B 1/0016; A61B 1/2676; A61M 16/0429; A61M 16/0488; A61M 25/0102; A61M 25/0133
See application file for complete search history.

(56) References Cited

U.S. PATENT DOCUMENTS

| | | | |
|---|---|---|---|
| 2005/0182295 A1* | 8/2005 | Soper | A61B 1/2676 600/117 |
| 2007/0197896 A1 | 8/2007 | Moll et al. | |
| 2009/0322867 A1* | 12/2009 | Carrey | A61B 1/00042 348/E7.085 |
| 2011/0077466 A1* | 3/2011 | Rosenthal | A61B 1/00096 600/188 |
| 2011/0137127 A1 | 6/2011 | Schwartz | |
| 2011/0245609 A1 | 10/2011 | Laser | |
| 2012/0078055 A1 | 3/2012 | Berci | |
| 2012/0089014 A1 | 4/2012 | Sabczynski | |
| 2014/0160261 A1* | 6/2014 | Miller | A61B 1/05 348/77 |
| 2015/0059736 A1 | 3/2015 | Qiu | |
| 2015/0099935 A1 | 4/2015 | Runnels | |
| 2015/0313452 A1* | 11/2015 | Hasser | A61B 34/35 600/102 |
| 2015/0319410 A1* | 11/2015 | Gu | G01N 21/954 348/82 |
| 2016/0081539 A1* | 3/2016 | Pagan | A61B 1/00154 600/184 |
| 2016/0095506 A1* | 4/2016 | Dan | A61B 1/045 600/188 |
| 2016/0250432 A1* | 9/2016 | Hendrix | A61B 1/05 600/188 |
| 2016/0278611 A1 | 9/2016 | Power | |
| 2016/0279365 A1* | 9/2016 | Esnouf | A61M 16/0418 |
| 2017/0164869 A1 | 6/2017 | Lee | |
| 2017/0291001 A1* | 10/2017 | Rosenblatt | A61B 5/6852 |
| 2018/0110950 A1* | 4/2018 | Runnels | A61B 1/05 |
| 2018/0147381 A1 | 5/2018 | Chen | |
| 2018/0221610 A1 | 8/2018 | Larson | |
| 2018/0250484 A1* | 9/2018 | McCormick | A61B 1/05 |
| 2018/0338675 A1* | 11/2018 | Eggli | A61B 1/267 |
| 2019/0082932 A1* | 3/2019 | Schoonbaert | A61B 1/00052 |
| 2019/0380781 A1* | 12/2019 | Tsai | A61B 1/267 |
| 2020/0054849 A1* | 2/2020 | Venticinque | A61M 16/0497 |
| 2020/0107701 A1 | 4/2020 | Gliner | |
| 2020/0214538 A1 | 7/2020 | Pesach | |
| 2020/0254204 A1 | 8/2020 | Moffat et al. | |
| 2021/0220594 A1 | 7/2021 | Biro | |

OTHER PUBLICATIONS

Lee, Hyung-Chul, et al.; "Real-time endoscopic image orientation correction system using an accelerometer and pyrosensor," Plos One, 12(11), Nov. 3, 2017, 12 pgs.

* cited by examiner

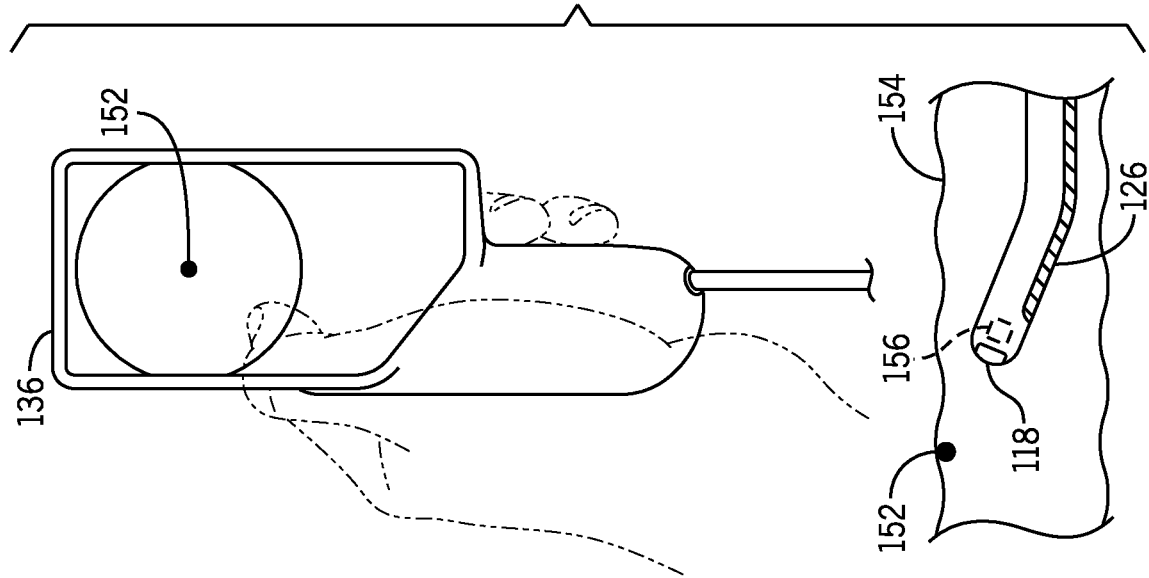
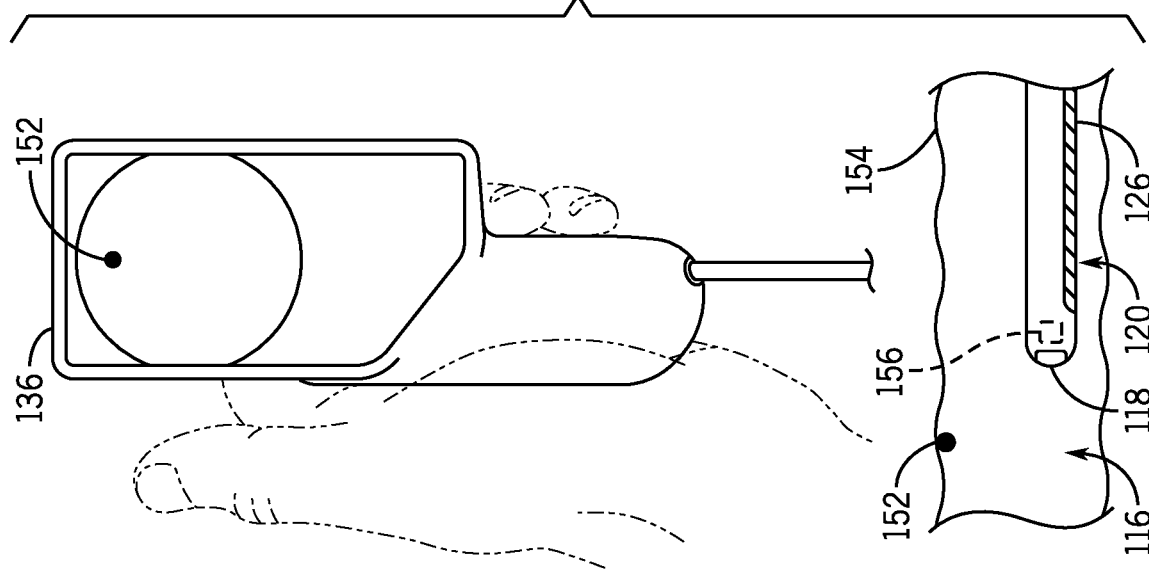

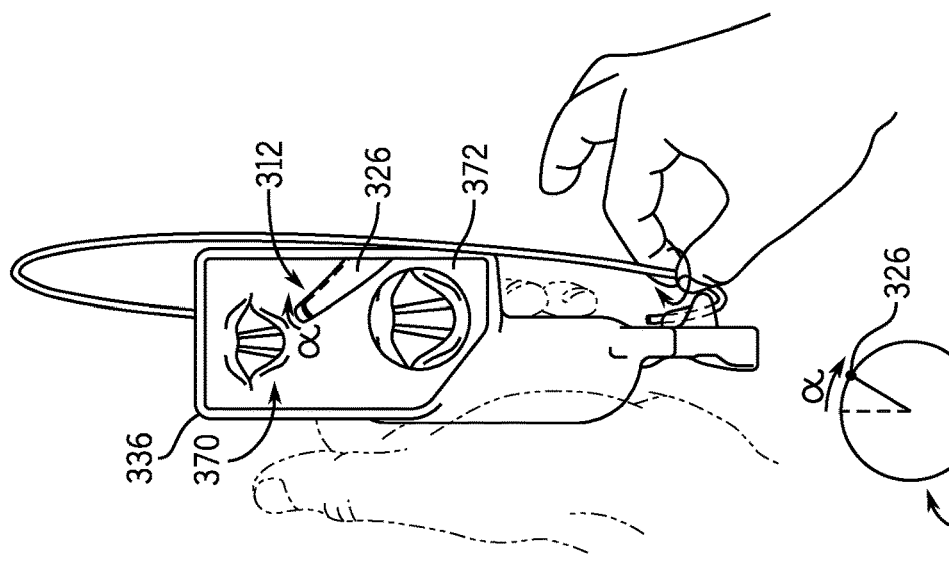
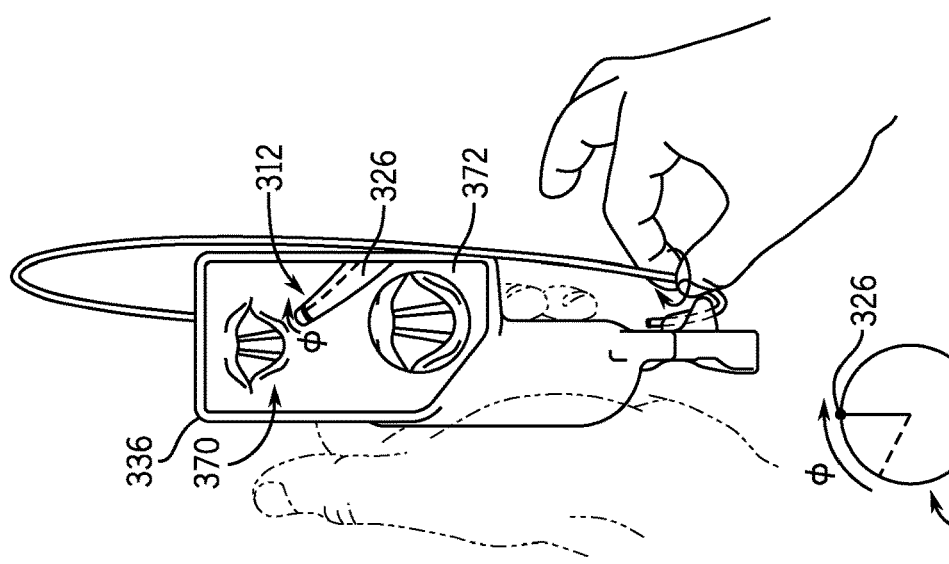
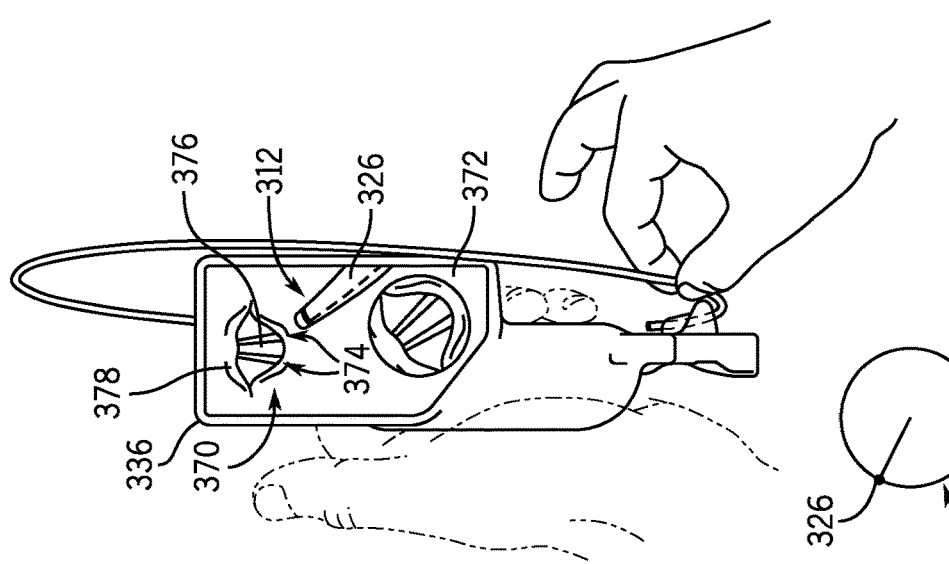

MULTIFUNCTIONAL VISUALIZATION INSTRUMENT WITH ORIENTATION CONTROL

CROSS-REFERENCE TO RELATED APPLICATIONS

This application is a division of U.S. patent application Ser. No. 16/802,242 filed on Feb. 26, 2020, which claims the benefit of U.S. Provisional Application No. 62/812,678 filed on Mar. 1, 2019, the disclosures of which are herein incorporated by reference in their entireties. To the extent appropriate a claim of priority is made to both applications.

BACKGROUND

The present disclosure relates generally to medical devices and, more particularly, to a method of controlling a steerable introducer, such as a flexible endoscope.

Introducers are long flexible instruments that can be introduced into a cavity of a patient during a medical procedure, in a variety of situations. For example, one type of introducer is a flexible endoscope with a camera at a distal end. The endoscope can be inserted into a patient's mouth or throat or other cavity to help visualize anatomical structures, or to help perform procedures such as biopsies or ablations. Another type of introducer is a blind bougie (with no camera) which may be inserted and then used to guide another device (such as an endotracheal tube) into place. These and other introducers may include a steerable distal tip that can be actively controlled to bend or turn the distal tip in a desired direction, to obtain a desired view or to navigate through anatomy. However, these steerable introducers can be difficult to maneuver into the desired location and orientation within a patient's anatomy.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a multifunctional laryngoscope includes a handle, a display screen on the handle, and a camera stick at the distal end of the handle. The camera stick has an arm and a camera. The laryngoscope also includes a steering input for steering an introducer, located on the handle or the display screen processor within the laryngoscope is programmed to execute instructions for receiving from the steering input a steering command in a first reference frame, and mapping the steering command to a second reference frame oriented to a distal end of the introducer.

In an embodiment, an endoscope controller includes a handle, a display screen on the handle, an endoscope port located on the handle or the display screen, and a user input located on the handle or the display screen. A processor within the controller is programmed to execute instructions for receiving from the user input a steering command in a user reference frame, receiving, from an endoscope coupled to the endoscope port, an orientation signal from an orientation sensor at an endoscope distal end, and translating the steering command as a function of the orientation signal.

In an embodiment, a method for controlling a steerable introducer includes receiving, at a processor, an orientation signal from an orientation sensor located at a distal end of a steerable introducer. The orientation signal defines an angular orientation of the distal end of the introducer. The method also includes receiving, at the processor, a steering command comprising a steering direction in a user reference frame, translating the steering command from the user reference frame to the angular orientation of the distal end of the introducer, and steering the distal end of the introducer according to the translated steering command.

In an embodiment, a method for controlling a steerable introducer includes receiving, at a processor, a steering command from a user input and an orientation signal from an orientation sensor of a steerable introducer. The method also includes translating, at the processor, the steering command as a function of the orientation signal, and steering the introducer according to the translated steering command.

In an embodiment, a method for controlling a steerable introducer includes receiving, at a processor, a steering command from a user input and an orientation input from an orientation sensor. The method also includes generating, at the processor, a variable steering signal comprising steering instructions that vary as a function of both the steering command and the orientation input, and steering the introducer according to the variable steering signal.

In an embodiment, a method includes receiving, at a processor, a laryngoscope image from a laryngoscope camera; receiving, at the processor, an endoscope image from an endoscope camera at a distal end of an endoscope and an orientation signal from an orientation sensor at the distal end of the endoscope; receiving a user input to establish a reference frame of the distal end; receiving an updated signal from the orientation sensor that indicates that the distal end has rotated away from the reference frame; and rotating an updated endoscope image into the reference frame based on the updated signal.

Features in one aspect or embodiment may be applied as features in any other aspect or embodiment, in any appropriate combination. For example, any one of system, laryngoscope, controller, introducer, or method features may be applied as any one or more other of system, laryngoscope, controller, introducer, or method features.

BRIEF DESCRIPTION OF THE DRAWINGS

Advantages of the disclosed techniques may become apparent upon reading the following detailed description and upon reference to the drawings in which:

FIG. 3A is a schematic view of an image frame associated with a first introducer orientation, in accordance with certain embodiments of the disclosure.

FIG. 3B is a schematic view of an image frame associated with a second introducer orientation, in accordance with certain embodiments of the disclosure.

FIG. 6A is a schematic view of an image frame associated with a first introducer orientation, in accordance with certain embodiments of the disclosure.

FIG. 6B is a schematic view of an image frame associated with a second introducer orientation, in accordance with certain embodiments of the disclosure.

FIG. 6C is a schematic view of an image frame associated with a third introducer orientation, in accordance with certain embodiments of the disclosure.

DETAILED DESCRIPTION OF SPECIFIC EMBODIMENTS

One or more specific embodiments of the present techniques will be described below. According to an embodiment, a system is provided for accessing patient anatomy with a steerable introducer, and for adjusting steering commands according to an orientation of the introducer. As the introducer is passed into a patient, the user may rotate or turn the distal tip of the introducer in order to maneuver through the patient's anatomy or to obtain a desired view. When the introducer is rotated or turned multiple times during a procedure, it can be difficult for the user to keep track of the changed orientation of the introducer's distal end. Subsequently, the user may inadvertently bend or turn the introducer in the wrong direction. For example, a user may intend to steer the introducer to the user's right, but because the introducer is rotated from its default position, the result of this command is for the introducer to bend to the user's left.

The disclosed embodiments use orientation information of the introducer to account for differences between the orientation of the distal end of the introducer and the user's own frame of reference. As a result, an introducer steering system using the orientation information provides more intuitive viewing of images captured by the introducer and/or more intuitive steering of the distal end of the introducer within the handle. Further, because the orientation information is not harvested from a hand-held device that is manipulated by the operator, operator variability in the position or angle of the hand-held device during use will not contribute to inaccurate orientation information.

Figure 1:
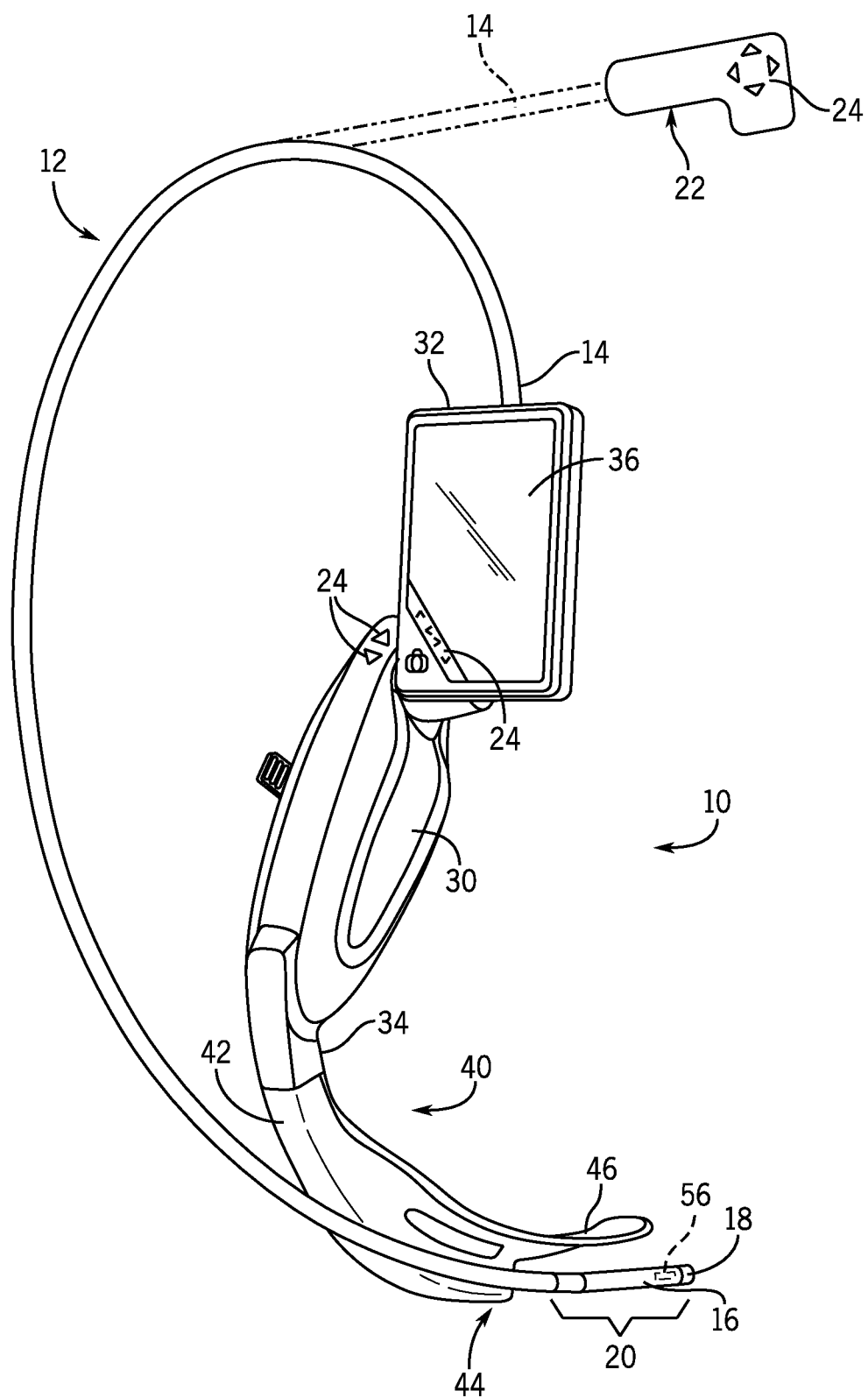
FIG. 1 is a perspective view of a multifunctional controller and steerable introducer of a steerable introducer system, in accordance with certain embodiments of the disclosure.

Accordingly, in an embodiment, an introducer steering system translates steering commands from the user's reference frame into the orientation of the introducer, to preserve the user's intention in steering the introducer. An embodiment of a steerable introducer system is depicted in FIG. 1. The system includes a video laryngoscope 10 and a steerable introducer 12. An introducer is a thin, elongated, flexible instrument (which may be relatively narrower, more flexible, and longer compared to a laryngoscope or an endotracheal tube) that can be inserted into a handle cavity for exploration, imaging, biopsy, or other clinical treatments, including catheters, endoscopes (with a camera), blind bougies (without a camera), or other types of scopes or probes. Introducers may be positioned to extend into the airway and be steered into the airway passage (such as the pharynx, larynx, trachea, or bronchial tubes) by the user via advancement of the distal end to a desired position and, in certain embodiments, subsequent rotation or repositioning of the introducer. Introducers may be tubular in shape.

The introducer 12 includes a proximal end 14 (nearest the user) and an opposite distal end 16 (nearest the patient), and in this example a camera 18 positioned at the distal end, for viewing the patient's anatomy. The introducer 12 includes a distal steerable portion 20 which can bend, twist, turn, or rotate. The distal steerable portion 20 may move within two dimensions (in a plane) or within three dimensions of space. The distal steerable portion 20 is steered by a steering system. The steering system may include one or more memory metal components (e.g., memory wire, Nitinol wire) that changes shape based on electrical input, a piezoelectric actuators (such as the SQUIGGLE motor from New Scale Technologies, Victor NY), a retractable sheath (retractable to release a pre-formed curved component such as spring steel which regains its curved shape when released from the sheath), mechanical control wires, hydraulic actuators, servo motors, or other means for bending, rotating, or turning the distal end or components at the distal end of the introducer.

The proximal end 14 of the introducer 12 connects to a controller, which may be a reusable or single-use disposable handle 22, or a multi-purpose medical device such as the video laryngoscope 10. The video laryngoscope 10 includes a handle 30 with a proximal end 32 and distal end 34. The handle 30 includes a display screen 36 mounted on a proximal side of a grip or handle 30.

The controller operates the steering system to steer the steerable portion 20 of the introducer, and includes a user input 24 to receive steering commands from the user. As shown in FIG. 1, the user input 24 may include buttons on the handle 22 or on the video laryngoscope 10. The user presses the buttons to indicate which direction to turn or steer the introducer. The user input 24 may be located on the display screen 36, on the grip 30, or both. The user input 24 may be one or more physical buttons (or switch, lever, joystick, or similar input), touch-sensitive graphics or icons on a touch screen (such as on the screen 36), a keyboard, or other suitable user input.

As shown in FIG. 1, the video laryngoscope includes a camera stick 40 extending from the distal end 34 of the handle 30. The camera stick 40 includes an elongated arm 42 carrying a camera 44 at its distal end. The camera stick 40 fits inside a removable, disposable, transparent blade 46. More information about laryngoscope blades can be found, for example, in Applicant's U.S. Pat. Nos. 9,775,505 and 9,066,700. Images from the video laryngoscope camera 44 and/or from the introducer camera 18 (if present) are displayed on the display screen 36.

In an embodiment, as shown in FIG. 1, the steerable introducer 12 includes an orientation sensor 56 at the distal tip of the introducer. The orientation sensor 56 may be an inertial measurement unit (IMU), accelerometer, gyroscope, or other suitable sensor. The orientation sensor 56 is located inside the tubular housing of the introducer 12. In an embodiment, the orientation sensor 56 is located very close to the terminus of the distal end 16 of the introducer, and may be co-located with the camera 18 (if present), to enable the orientation sensor 56 to capture much of the full range of movement of the distal end 16 and the camera 18. In an embodiment, the orientation sensor 56 is placed at (e.g., positioned on or in) the distal end 16 of the steerable portion 20, remote from the proximal end of the steerable portion 20, to place the orientation sensor 56 away from the fulcrum of movement of the distal end 16 and camera 18.

The disclosed embodiments that include the orientation sensor 56 at or near the distal end 16 of the introducer 12 provide more accurate orientation information relative to implementations in which the orientation information is derived from an orientation sensor in the controller (such as the video laryngoscope, wand, or handle). In such an example, information derived from a sensor located in the controller relies on an assumption that the orientation of the controller is the same as the orientation of the distal tip. To maintain the conditions for that assumption, the user may be instructed to hold the controller at a particular angle or position during operation. However, user variability in controller positioning during operation may lead to inaccuracies in the reported orientation information. Accordingly, orientation information measured at a handheld device located proximally of the introducer may not provide accurate information. Further, movement measured at the controller may not translate into corresponding movement of the distal tip. For example, the handle of the introducer may have a degree of compliance, so rotation by the user at the proximal end is not perfectly transferred along the length of the introducer. As another example, along a tortuous path through a patient's anatomy, torsion and friction can create losses in rotation. In an embodiment disclosed herein, the orientation sensor 56 positioned at or near the distal end 16 of the introducer 12 provides more accurate orientation information than controller-based measurement of orientation.

As provided in the disclosed embodiments, accurate orientation information captured at or near the distal end of an introducer 12 permits active image adjustment, providing more intuitive visualization of introducer images and, in turn, more intuitive steering within an established frame of reference that can be oriented to gravity or to a userdefined frame of reference. Further, the introducer is steered at the distal end 16 without physical rotation of the proximal end, rather than implementations in which distal rotation and orientation change is driven by torsional force translated from the proximal end 14 to the distal end 16. These introducer uses a steering system that is effective at the distal tip (such as push or pull wires) to bend the distal tip in a desired direction, even when the length of the introducer between the proximal and distal ends is slack; the introducer does not require torsional force to translate along the introducer housing from the proximal to the distal end. The introducer does not need to be straight or taught in order to translate steering inputs to the distal end. Distal bending and movement of the introducer is accomplished independent of the orientation, position, or movement of the proximal end of the introducer; steering is not physically coupled between the proximal end (such as the handle) and the distal end. Further, the introducer system does not need to make any assumptions about how much torsional force was successfully translated (or lost) along the length from the proximal to distal end; rather, an orientation sensor at the distal tip provides an orientation signal that indicates the current orientation of the distal tip. In this manner, the structure of the introducer 12 may be less torsionally stiff relative to implementations in which the steering relies on torsional force transfer. Accordingly, in an embodiment the introducer 12 is an extruded structure with low torsional stiffness (low enough that torsional rotation does not translate from the proximal to the distal end). In an embodiment, the introducer is a non-braided structure, such as an extruded polymer. In an embodiment, the introducer is an extruded structure devoid of torsional stiffeners such as braided wires or braided structures.

Figure 2:
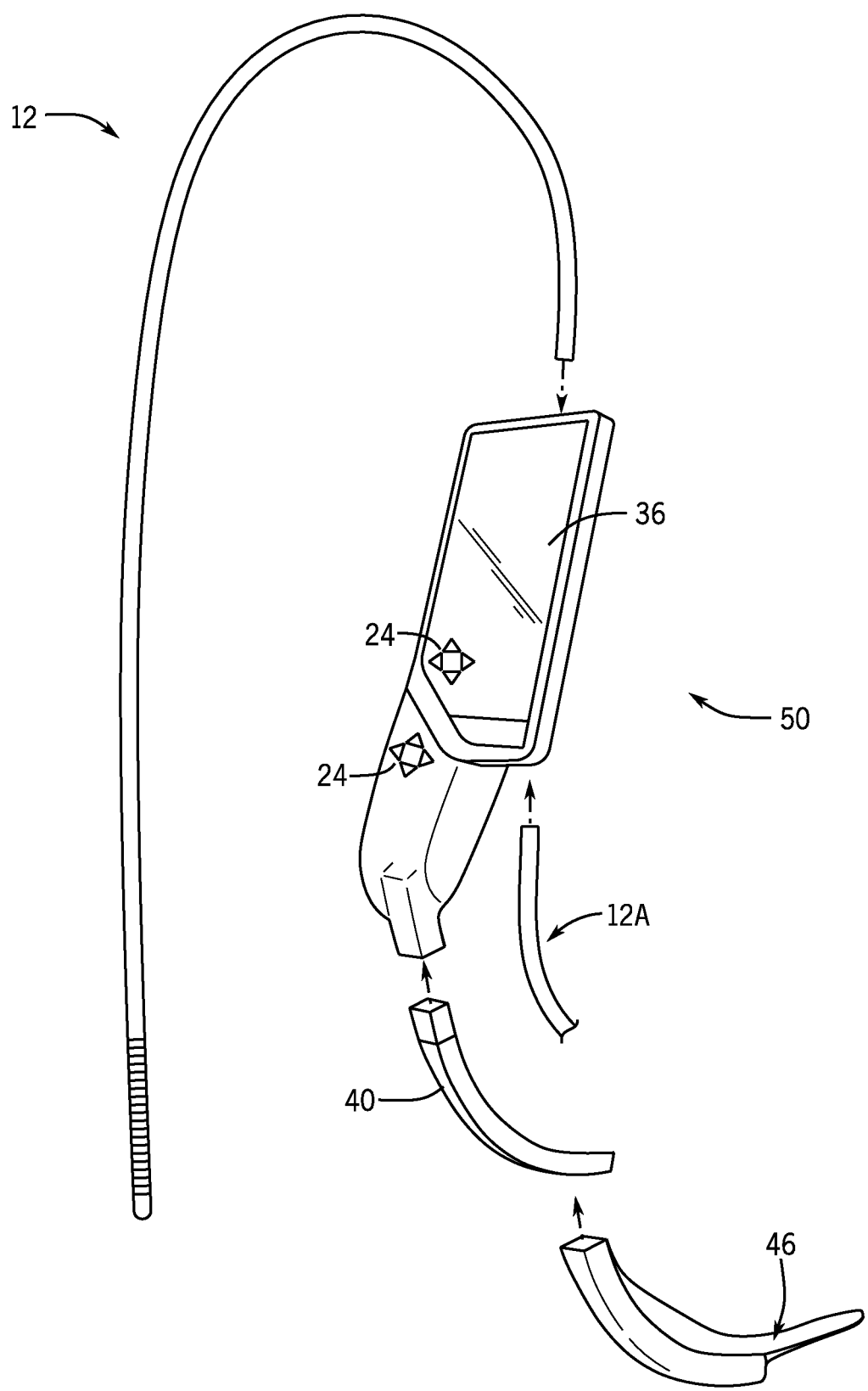
FIG. 2 is a perspective view of a visualization wand and steerable introducer of a steerable introducer system, in accordance with certain embodiments of the disclosure.

FIG. 2 shows another embodiment in which the controller is a wand 50, similar to the video laryngoscope 10 but without the camera stick 40. The wand 50 includes the user input 24 to receive steering commands from the user, and includes the display screen 36. As shown in FIGS. 1 and 2, the controller may take the form of a handle 24, video laryngoscope 10, or wand 50 with integrated display screen 36. The controller can also take the form of a separate (not integrated) touch screen display, located in the room (such as mounted on a cart or stand), spaced apart from the introducer. This touch screen communicates user inputs via a wired or wireless connection to the introducer. In one embodiment, the handle 24 is integrated with the tubular introducer 12, and the entire device is single use and disposable. In another embodiment, the introducer is a two-part system, and the controller (handle, wand, laryngoscope, or other device) is removable from the introducer 12. The introducer 12 is then discarded after use, and the controller is retained and used again with a new tubular introducer. The controller houses power, display, steering control, and other functionality. In this manner, the endoscope introducer many be disposable while the relatively more costly and complex controller may be reused.

The introducer 12 can attach to the wand 50 from a top (proximal) end of the wand (such that the introducer extends up over the top of the screen), or from a bottom (distal) end of the wand (such that the introducer extends below away from the bottom of the screen). The introducer 12A in FIG. 2 is shown to indicate the option to connect the introducer to the wand 50 from below the screen.

FIG. 3A and FIG. 3B depict a method of steering an introducer, including translating steering commands from a user into executable actuator controls within the orientation of the introducer. For example, in FIGS. 3A-B, the introducer is a tubular endoscope 120 with a camera 118 located at its distal end 116. The endoscope 120 also has a feature—such as an orientation indicator, a working channel, a surgical tool, a light source, or other instrument—that is located at one angular position around the tubular endoscope. In FIG. 3A-B, this feature is an orientation marker 126, which is a visible indicia or marker that indicates to the user which direction is up for the steering controls. The marker 126 can be formed by printed graphics, a groove or other three-dimensional feature, a glow-in-the-dark ink or indicia, or an actively powered light (such as a small LED strip or light). The marker 126 is located on a top side of the endoscope 120, when the endoscope is in its default, resting position (not bent, twisted, or steered). In image A, the endoscope has been rotated 180 degrees from that position, such that the marker 126 is on the bottom of the endoscope.

A real-time image from the camera is shown on the display screen 136, which may be a display screen on a wand, a video laryngoscope, a monitor, or any other display screen in the medical facility. Images from the camera 118 may be transmitted through wired connections or wirelessly to the display screen 136. In FIG. 3A, the field of view of the endoscope camera includes an anatomical structure 152 inside a passage 154. In an example, the passage 154 is the trachea, and the structure 152 is a tumor. In other cases, the passage 154 is a gastrointestinal passage, a nasal canal, or any other anatomical lumen. The structure 152 can be a polyp, tumor, blood vessel, vocal cords, suture, stent, bifurcation of passages (such as bronchial passages, or the carina), or any other visible anatomical or medical feature.

In FIG. 3A, the structure 152 appears toward the top of the display screen 136. The user may decide to steer the endoscope 120 toward the structure 152, and give an "up"

steering command (such as through a user input 24). The user's steering command is based on the user's frame of reference, such as the directions in the image on the display screen. However, in this situation, the user's intention in steering "up" is not the same as the default resting "up" orientation of the endoscope. The orientation of the endoscope 120 has been changed with respect to the user's reference frame.

Accordingly, in an embodiment, the endoscope steering system translates the user's command into the endoscope's current orientation. In FIG. 3B, the user provides an "up" steering command which means to bend "up" in the frame of reference of the display screen 136. The steering system translates this for the endoscope such that the endoscope bends in a direction opposite the marker 126 (which is the "down" direction in the endoscope's default frame of reference). As shown in FIG. 3B, the endoscope bends toward the structure 152, and the structure 152 moves into the center of the screen 136.

Figure 5:
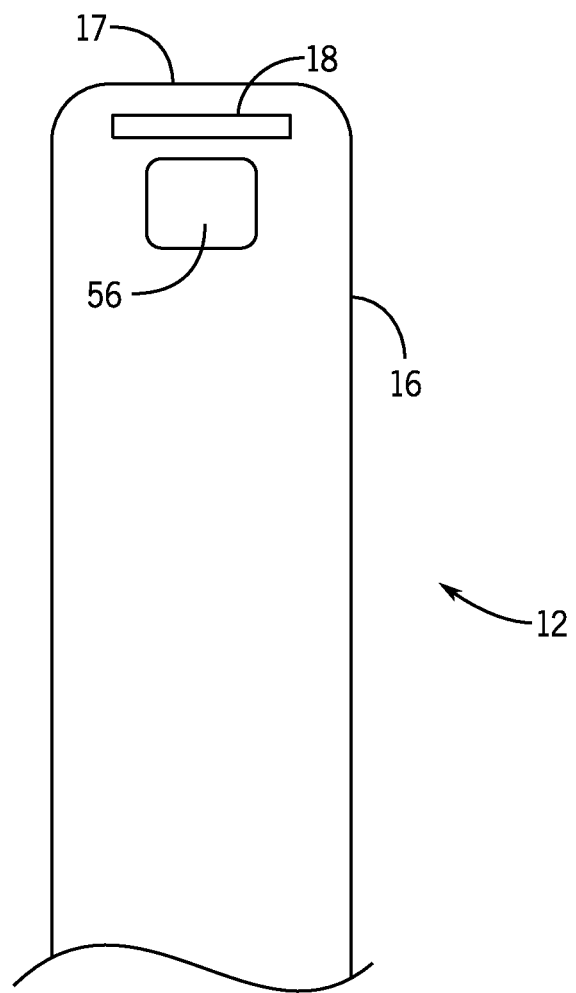
FIG. 5 is a cut-away top view of a distal end of a steerable introducer, in accordance with certain embodiments of the disclosure.

A schematic cut-away view of the distal end 16 of the introducer 12 is shown in FIG. 5. This figure shows the camera 18 positioned at the terminus 17 of the distal end 16 of the introducer 12, to obtain a clear view forward. The orientation sensor 56 is located just behind the camera 18. In an embodiment, the orientation sensor 56 is adjacent the camera 18. In an embodiment, the orientation sensor 56 is mounted on a flex circuit behind the camera 18. In an embodiment, the orientation sensor 56 is mounted on the same flex circuit as the camera 18, though the orientation sensor 56 and the camera 18 need not be in communication on the shared flex circuit. In an embodiment, the orientation sensor has a size of between 1-2 mm in each dimension. It should be understood that, in certain embodiments, the introducer 12 is blind and there is no camera 18 present.

The orientation sensor is an electronic component that senses the orientation or movement of the distal end of the introducer. The orientation sensor contains a sensor or a combination of sensors to accomplish this, such as accelerometers, magnetometers, and gyroscopes. The orientation sensor detects position and/or movement of the distal tip of the introducer and provides a signal indicating a change in the introducer's orientation. An orientation sensor 156 is also illustrated in FIG. 3A-B, located at the distal end 116 of the introducer 120, just behind the camera 118. In an embodiment, the signal from the orientation sensor is based on just the accelerometer (without utilizing other sensors such as a gyroscope or magnetometer). In an embodiment, an accelerometer is used as the orientation sensor.

Figure 4:
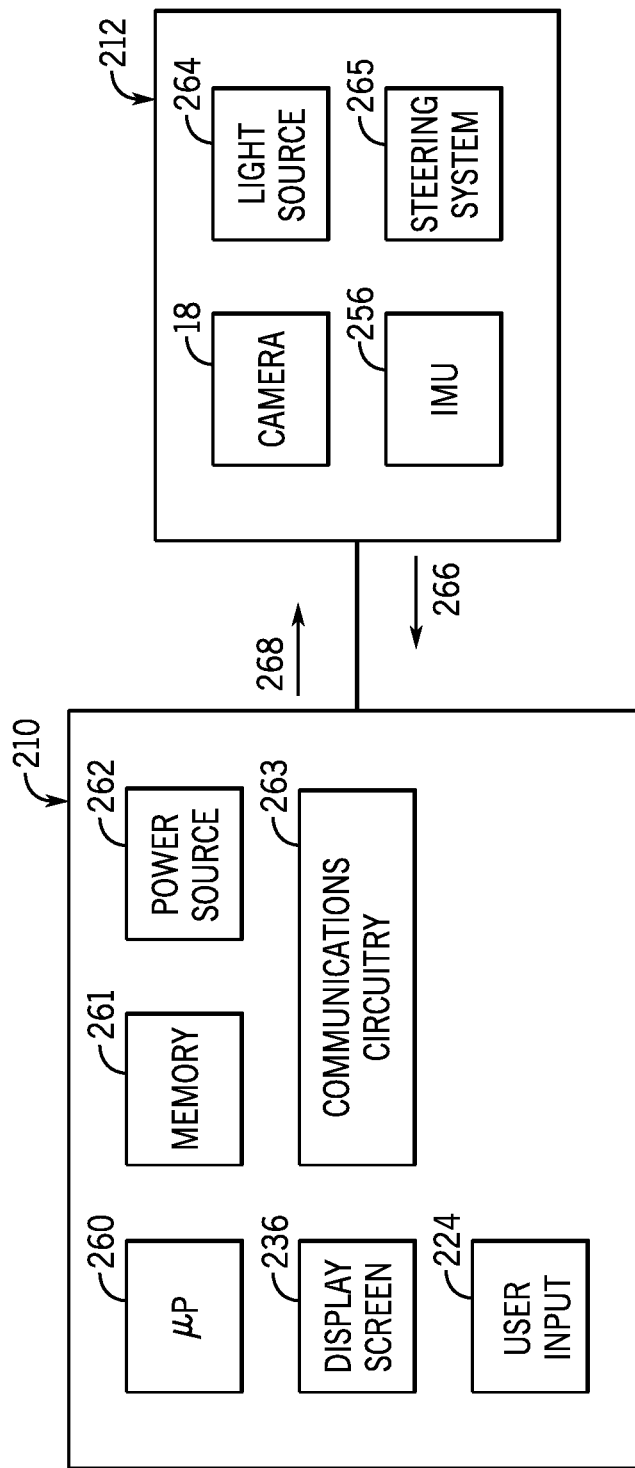
FIG. 4 is a system schematic of a controller and introducer, in accordance with certain embodiments of the disclosure.

A schematic diagram of electrical components of a steerable introducer system is shown in FIG. 4. In this embodiment, the system includes a controller 210 (such as a video laryngoscope, handle, or wand) and an introducer 212. The controller 210 includes a microprocessor 260, memory 261, power source 262, display screen 236, user input 224, and associated circuitry 263 (such as, for example, a wireless transceiver for receiving and communicating data). When the controller is a video laryngoscope, it also includes a camera and light source, among other components. The introducer 212 includes a camera 18 (if present), a light source 264, an orientation sensor 256, and a steering system 265.

As depicted in FIG. 4, an orientation signal 266 is passed from the introducer 212 (based on measurements from the orientation sensor 256) to the controller 210, and an actuation control signal 268 is passed from the controller 210 to the introducer 212. The orientation signal may be produced by the orientation sensor located at a distal end of the introducer. The orientation signal defines an angular orientation of the distal end of the introducer with respect to gravity.

The orientation signal 266 and steering commands from the user input 224 are sent to the processor 260, which translates the steering commands into the actuation control signal 268. The actuation control signal 268 operates the steering system by including specific executable instructions for the individual actuator(s) of the steering system 265 on the introducer, to bend, twist, or move the steerable portion 20 of the introducer.

Figure 7:
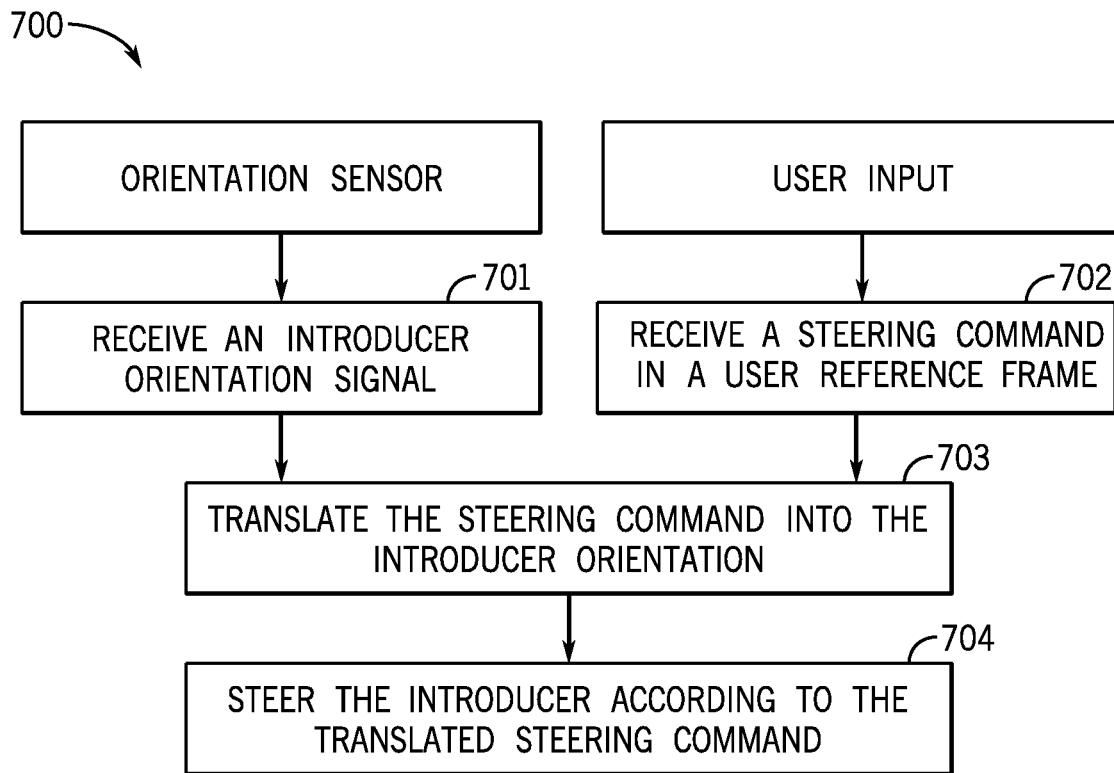
FIG. 7 is a flowchart of a method for steering an introducer, in accordance with certain embodiments of the disclosure.

A method 700 for controlling a steerable introducer, according to an embodiment, is depicted in FIG. 7. The method includes receiving, from an orientation sensor, an introducer orientation signal (at block 701). For example, the signal can be the orientation signal 266 from FIG. 4, received from an IMU or accelerometer or other sensor. The introducer orientation signal defines an angular orientation of the distal end of the introducer. The method also includes receiving, from a user input, a steering command in a user reference frame (at block 702). The method also includes translating the steering command from the user reference frame into the introducer orientation (at block 703). The method also includes steering the introducer according to the translated steering commands (at block 704). These steps can be done by a processor (such as processor 260) located inside an introducer controller (such as a laryngoscope, wand, or handle).

The user reference frame is the frame in which the user is giving steering directions. This reference frame could be aligned with the direction of gravity (so that a steering command of "down" means down toward the Earth). As another example, the reference frame could be aligned with an image on the display screen (so that a steering command of "down" means down in the image). As another example, the reference frame can be centered on a patient (so that a steering command of "down" means toward the patient's back, if the patient is lying on their side, or toward some other anatomical feature of the patient). These are just a few examples.

Figure 8:
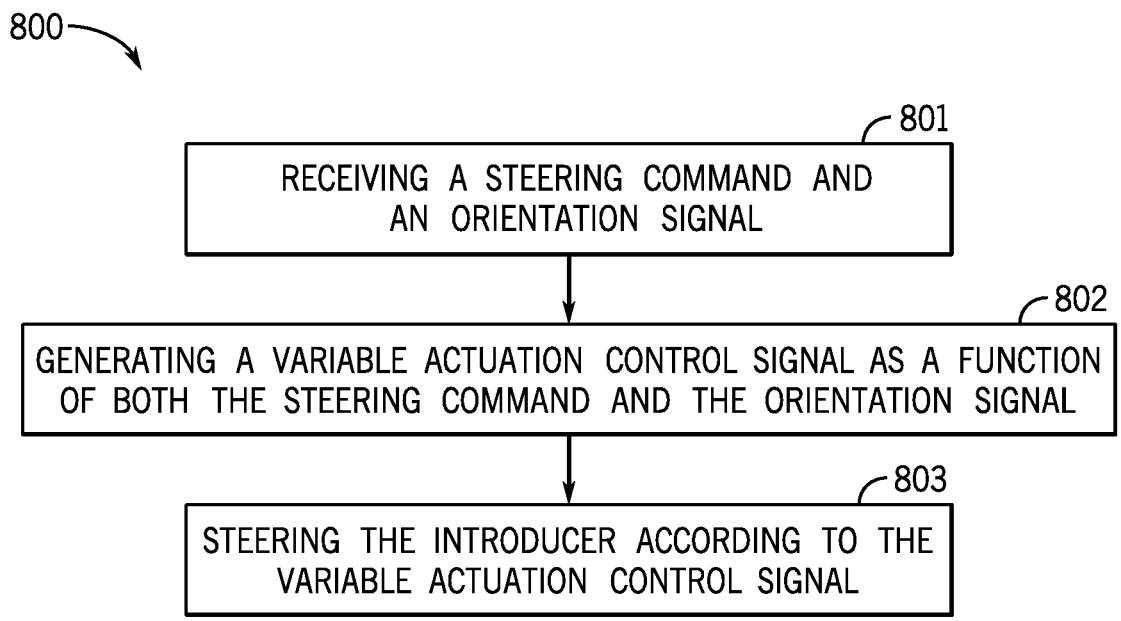
FIG. 8 is a flowchart of a method for steering an introducer, in accordance with certain embodiments of the disclosure.

Another example method 800 is outlined in FIG. 8. In this example, the method includes receiving a steering command and an orientation signal (at block 801). The method includes generating a variable actuation control signal as a function of both the steering command and the orientation signal (at block 802). The method includes steering the introducer according to the variable actuation control signal (at block 803). This can be done, for example, by a processor that generates an actuator control signal with specific instructions to operate the actuator(s) of the steering system of the introducer, to move the introducer in the direction specified by the user.

In this way, the actuation controls for the steering system are not tied to the introducer's internal frame of reference. Instead, the steering applied to the introducer is variable with the introducer's orientation. The same steering command from a user's frame of reference (for example, "up" toward the top of a display screen) will be translated into different actuator controls depending on how the introducer is oriented. Even with the same steering command from a user, the control signal that is sent to the actuator(s) of the steering control system of the introducer will vary with the introducer's orientation. For example, when the user inputs a command to bend "up" toward the top of the display screen, the steering control system may bend the introducer toward the orientation marker (such as 326), or away from the orientation marker, depending on how the introducer is oriented. Thus, the control signal that operates the steering control system of the introducer varies with the introducer's orientation as well as with the user's steering commands.

In an embodiment, the steering system includes two, three, four, or more actuators that control movement of the steerable tip of the introducer. In an embodiment, the steering actuation is accomplished by modeling the tip of the introducer as a circle, with the modeled actuators occupying discrete locations about the circumference of the circle. At these locations, the actuators act on the tip to bend or move the introducer. The circle is rotated according to the orientation signal from the orientation sensor, to indicate the orientation of the introducer with respect to the user's defined reference frame. Thus, when a user steering command is received (for example, bend "up" toward the top of the circle), the appropriate actions for each respective actuator can be determined. Each actuator is operated or energized proportionately according to its position on the circle with respect to the user command. It should be understood that the two or more actuators may be located at any position in the introducer and that correlates to a respective modeled circumferential location.

In an embodiment, the user can define a custom reference frame, as shown for example in FIGS. 6A-C, which illustrate a display screen 336 of a video laryngoscope displaying two images, a first image 370 from a camera on a video laryngoscope (such as camera 44 from FIG. 1), and a second image 372 from a camera on an endoscope 312 (such as camera 18 from FIG. 1). As shown in FIG. 6A-C, the endoscope 312 is located within the field of view of the laryngoscope camera, so the endoscope 312 is visible in the image 370. The endoscope includes an orientation marker 326 visible on a surface of the introducer 312. The lower panel of FIG. 6A is a schematic representation of a cross-section of the endoscope, with the orientation marker 326 shown at a top left position of the introducer 312.

The patient's vocal cords 374 and trachea 376 are visible in the images on the screen 336. However, the endoscope image 372 is rotated counter-clockwise, compared to the video laryngoscope image 370. Accordingly, a user may decide to manually rotate the endoscope to transition from the position in FIG. 6A into the position shown in FIG. 6B. In FIG. 6B, the user has rotated the endoscope clockwise by an angle. This rotation can be seen by the new position of the orientation marker 326. After rotation, the endoscope image 372 is aligned with the video laryngoscope image 370. At this point, the user may enter a command to establish the current orientation of the endoscope (in FIG. 6B) as the desired reference orientation or frame of reference. This can be done by pushing a button on the user input 24 or on a touch screen or other input. The controller then stores the endoscope's current orientation at the time of the user input as the reference frame for future adjustments. Subsequently, when the user gives steering commands (such as up, down, turn, etc.), those commands will be interpreted in this stored reference frame, and translated into movement of the endoscope based on the endoscope's orientation data. This enables the user to decide what reference frame to use for steering commands. For example, steering can be oriented to the patient's handle, instead of to gravity. While alignment with the laryngoscope image 370 is shown as an example, the user could choose any other orientation to establish the reference frame.

After establishing the position in FIG. 6B as the desired reference orientation, the system will correct steering and images to that reference orientation. For example, in FIG. 6C, the user has further rotated away from the position shown in FIG. 6B such that the introducer is rotated clockwise by angle $\alpha$. The introducer itself has rotated, as shown by the new position of the orientation marker 326 as seen in the laryngoscope image 370. However, the second image 372 (from the introducer) has not rotated. In FIG. 6C, the vocal cords and trachea remain upright, as they were oriented in FIG. 6B. The system accomplishes this by receiving information from the orientation sensor at the distal tip of the introducer, determining the amount of change (here, clockwise rotation by the amount of the angle $\alpha$), and reversing that movement to retain the image 372 in the same orientation as FIG. 6B. Similarly, steering controls entered by the user in FIG. 6B or FIG. 6C are interpreted according to the orientation of FIG. 6B, as described above. If the user instructs the introducer in FIG. 6C to steer "up" toward the top of the screen 336, the system will bend the introducer in that direction, even though the orientation marker 326 is rotated away from that position by the angle $\alpha$.

In another embodiment, the reference frame can be established by automatic image recognition. For example, returning to FIG. 6A-C, the processor on the controller may automatically recognize features in the image, such as the vocal cords 376 in both images 370 and 372, based on computer vision techniques. These techniques may include, for example, a single shot object detector (that can recognize anatomical structures), Haar feature-based cascade classifiers (to recognize anatomical structures), a neural net trained to output orientation based on known anatomy, landmark alignment with an ensemble of regression trees, object tracking once a useful feature is identified, or other computer vision techniques. The processor can then establish a reference frame based on the orientation of the vocal cords—for example, identifying "up" as toward the top of the vocal cords (such as toward the epiglottis 378). The processor can be programmed to recognize other anatomical structures (for example, the cross-sectional shape of the trachea, anterior vs. posterior positioning) and update or store the reference frame based on those structures. Image recognition can help align the user's reference frame with the patient anatomy, instead of with gravity.

In an embodiment, a user can transition from the dual-picture or picture-in-picture display (as shown in FIGS. 6A-C) to an introducer only (only image 372) display or laryngoscope only (only image 370) and vice versa. Based on the type of images or images displayed, the reference frame can be automatically adjusted. For example, alignment of the reference frame may be based on the orientation of the laryngoscope. Typically, the laryngoscope is positioned during use such that the image captured by the laryngoscope camera is oriented to gravity, with the top of the image on the display screen generally being "up" relative to gravity. However, certain procedures may involve different laryngoscope positioning relative to the patient, such as in the case of the user facing the patient and holding the laryngoscope rotated 180 degrees. In that case, the top of the laryngoscope image displayed on the display screen would actually correspond to a "down" direction relative to gravity. To account for different positioning or alignment of the laryngoscope relative to gravity, the alignment may be based on alignment to the laryngoscope image, which may or may not be aligned to gravity. However, upon a change of display mode to introducer-only display, the reference frame can automatically switch to a gravity-based alignment, which is determined by the orientation signal of the orientation sensor. Further, in an embodiment, the techniques may be used to establish a reference frame for steering commands when the introducer is blind (e.g., blind bougie) and no camera image is displayed. Nonetheless, the steering commands can be translated to a gravity-based or user-established reference frame and translated using the orientation signal information from the orientation sensor.

In FIG. 6B, the processor can also determine that the endoscope image 372 is rotated with respect to the video laryngoscope image 370 by the angle θ. In an embodiment, the processor corrects the endoscope image 372, rotating the image to align it with the video laryngoscope image 370, even without rotating the actual endoscope. This step keeps the two images aligned so that the user can more easily view them at the same time.

In an embodiment, the orientation signal 266 (FIG. 4) is used to adjust the displayed endoscope image (such as image 372, or on any other display screen). The processor 260 may use the signal 266 to automatically adjust the displayed image to a desired orientation, such as adjusting the image to make sure that the upward direction (anterior, toward the patient's chest) remains upward (toward the top proximal surface) on the display screen, even when the endoscope is rotated or turned inside the patient. As an example, the user may rotate the endoscope clockwise degrees (or any amount), as shown in FIG. 6C, such as to better position the endoscope within the patient's anatomy. In FIG. 6C, the image on the display screen remains stationary, even when the endoscope is rotated. The orientation sensor 256 at the tip or distal end of the endoscope registers the rotation, and the microprocessor 260 rotates the image on the screen in the reverse direction (in this example, counter-clockwise) by the same amount. If the endoscope is rotated again, in either direction, the microprocessor again compensates, so that the image on the screen remains oriented with the patient's anterior pointed upward on the display screen. In another embodiment, the microprocessor 260 receives realtime updated signals from the orientation sensor 256 indicating the relationship between the distal tip and gravity, so that the microprocessor can continually adjust the image to keep the direction of gravity pointed downward on the laryngoscope display screen, even as the endoscope itself is rotated.

Figure 9:
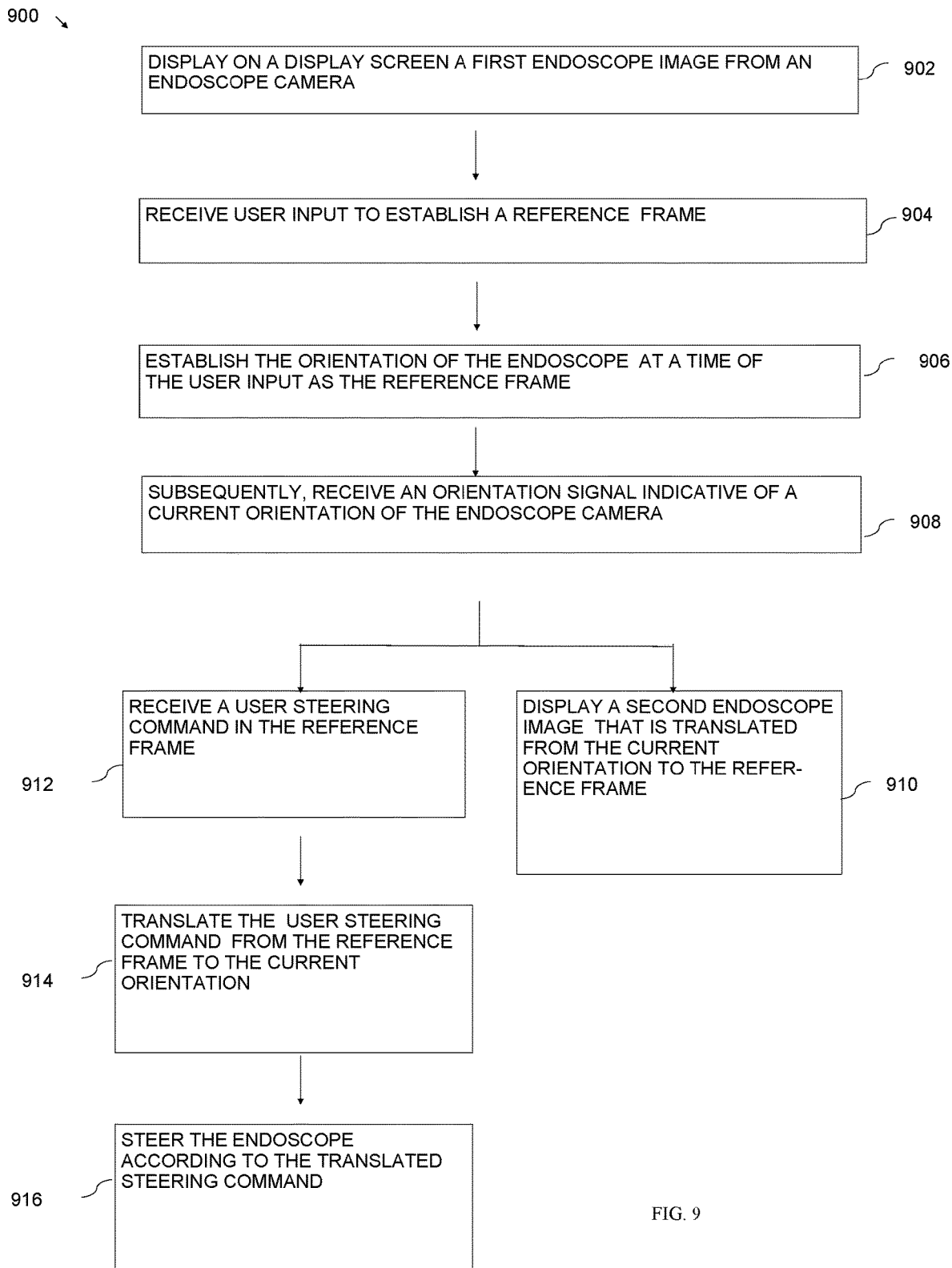
FIG. 9 is a flowchart of a method for adjusting introducer orientation to a frame of reference, in accordance with certain embodiments of the disclosure.

An example method 900 is outlined in FIG. 9 that may be used in conjunction with a picture-in-picture display or dual-picture display of a multifunctional visualization instrument with steering control (e.g., a video laryngoscope 10, see FIG. 1). In this example, the method includes displaying an image (e.g., an image 372, see FIG. 6A-C) from an endoscope camera of an endoscope on a display screen (block 902). Optionally, the method may also display a first video laryngoscope image (e.g., an image 370, see FIG. 6A-C) from a laryngoscope camera of a video laryngoscope. A user can define a custom reference orientation or reference frame (block 904) via a user input or, alternatively, the system may automatically establish a reference frame based on gravity or image processing. The orientation of the endoscope at the time of the user input is established as the reference frame (block 906). That is, when using a user input to define the reference frame, the orientation of the endoscope at the time of user input is flagged or stored as the reference frame orientation. The orientation sensor subsequently provides a current orientation signal that indicates that the endoscope distal end, which includes the endoscope camera, has a different orientation than the reference frame (block 908). For example, the current orientation of the distal end may change as a result of user manipulation or steering events to move (e.g., rotate) away from the orientation associated with the reference frame to a current orientation. Accordingly, a subsequent or second endoscope image captured at the current orientation is translated from the current orientation (e.g., modified, rotated) to the reference frame (block 910). In an embodiment, any received steering command (block 912) received at the updated orientated is translated from the updated orientation to the reference frame (block 914) based on the amount and direction of rotation to facilitate steering of the endoscope according to the translated steering command (block 916).

A user can also update the reference orientation throughout a procedure. For example, the steps outlined in FIG. 9 can be repeated to enable the user to establish a new reference orientation. For example, if a patients shifts, is rotated, sits up or lies down, coughs, etc., the clinical user may decide to establish a new reference orientation for the introducer, such that the system will rotate image information from the introducer to keep the images stationary in this reference orientation and translate steering commands from the user to the introducer. In an embodiment, the system establishes an automatic or default orientation (such as gravity down), and the user can override or change this default orientation by establishing a new reference orientation as outlined in FIG. 9.

An introducer with variable steering may be used to assist with endotracheal intubation. During endotracheal intubation, clinicians (such as an anesthesiologist or other medical professional) attempt to navigate an endotracheal tube through a limited view through the patient's mouth. Clinicians may rely on the relative position of anatomical structures to navigate. During intubation, the arytenoid cartilage proves useful as an anatomical landmark; the vocal cords are anterior to the arytenoid cartilage, the esophagus posterior. In an embodiment of the present disclosure, the anterior direction is aligned with the top of the user's display screen and set as the reference orientation, so that anterior is maintained as "up" on the screen. During intubation, the user can input a command to steer an introducer "up" to pass the tip over the arytenoids and into the vocal cords. Then, the user can pass an endotracheal tube over the introducer and ensure that the endotracheal tube passes into the trachea, rather than the esophagus. By contrast, if the user becomes disoriented and inadvertently steers the introducer into the esophagus (instead of the trachea), esophageal intubation can result, causing serious complications for the patient. Accordingly, a system in which the user's orientation is maintained, and steering inputs are translated accordingly, can improve clinical practice.

While the present techniques are discussed in the context of endotracheal intubation, it should be understood that the disclosed techniques may also be useful in other types of airway management or clinical procedures. For example, the disclosed techniques may be used in conjunction with secretion removal from an airway, arthroscopic surgery, bronchial visualization (bronchoscopy), tube exchange, lung biopsy, nasal or nasotracheal intubation, etc. In certain embodiments, the disclosed multifunctional visualization instruments may be used for visualization of anatomy (stomach, esophagus, upper and lower airway, ear-nose-throat, vocal cords), or biopsy of tumors, masses or tissues. The disclosed multifunctional visualization instruments may also be used for or in conjunction with suctioning, drug delivery, ablation, or other treatments of visualized tissue. The disclosed multifunctional visualization instruments may also be used in conjunction with endoscopes, bougies, introducers, scopes, or probes.

In operation, a caregiver may use a laryngoscope to assist in intubation, e.g., to visualize a patient's airway to guide advancement of the distal tip of an endotracheal tube through the patient's oral cavity, through the vocal cords, into the tracheal passage. Visualization of the patient's anatomy during intubation can help the medical caregiver to avoid damaging or irritating the patient's oral and tracheal tissue, and avoid passing the endotracheal tube into the esophagus instead of the trachea. The laryngoscope may be operated with a single hand (such as the user's left hand) while the other hand (such as the right hand) grips the endotracheal tube and guides it forward into the patient's airway. The user can view advancement of the endotracheal tube on the display screen in order to guide the endotracheal tube into its proper position.

While the video laryngoscope can facilitate more efficient intubation than direct-view intubation, certain patients may benefit from visualization and/or steering devices that extend further into the airway than a laryngoscope. For example, patients with smoke inhalation, burns, lung cancer, and/or airway traumas may benefit from visualization past the vocal cords, which is not accomplished with a laryngoscope. Such visualization may be beneficial for endoscopic placement of endotracheal tubes and/or placement or positioning of suctioning devices in the airway. Endoscope placement (e.g., with an endotracheal tube loaded into the endoscope) may be helpful for anterior or challenging airways. For example, patients whose anatomy cannot be suitably manipulated (either through head positioning or laryngoscopy) to create space for passage of an endotracheal tube may benefit from imaging devices that go beyond the visualization range of a laryngoscope and that provide a greater steering range for a camera, or from articulating devices that can be manipulated and moved within the visualization range of the laryngoscope.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

The invention claimed is:

1. A steerable-introducer controller, comprising:
   a handle comprising a proximal end and a distal end;
   a display screen on the handle;
   an introducer port supported by the handle or the display screen and connectable to an introducer;
   a user input located on the handle or the display screen; and
   a processor within the controller, programmed to execute instructions for:
   receiving, from the user input, a steering command to steer the introducer, the steering command being in a user reference frame;
   receiving, through the introducer port, an orientation signal from the introducer;
   translating the steering command as a function of the orientation signal; and
   steering the introducer according to the translated steering command by controlling a steering wire system at least partially within the introducer.

2. The steerable-introducer controller of claim 1, wherein the orientation signal is from an inertial measurement unit (IMU) located at a distal tip of the introducer.

3. The steerable-introducer controller of claim 1, wherein the orientation signal defines an angular orientation of a distal tip of the introducer with respect to gravity.

4. The steerable-introducer controller of claim 1, wherein the user reference frame is different from a reference frame of a distal tip of the introducer.

5. The steerable-introducer controller of claim 1, wherein the processor is further programmed to execute instructions for:
   receiving an image from a camera of the introducer; and
   displaying the image on the display screen in the user reference frame.

6. The steerable-introducer controller of claim 5, wherein the steerable-introducer controller is a video laryngoscope including a camera, and the processor is further programmed to execute instructions for:
   receiving an image from the camera of the video laryngoscope;
   displaying the image from the camera of the video laryngoscope concurrently with the image from the camera of the introducer.

7. A steerable-introducer controller, comprising:
   a handle;
   a display screen on the handle;
   an introducer port;
   a user input located on the handle or the display screen; and
   a processor within the controller, programmed to execute instructions for:
   receiving, from the user input, a steering command to steer an introducer, the steering command being in a user reference frame;
   receiving an orientation signal from the introducer;
   translating the steering command as a function of the orientation signal; and
   steering the introducer according to the translated steering command by controlling a steering wire system at least partially within the introducer.

8. The steerable-introducer controller of claim 7, wherein the orientation signal is from an inertial measurement unit (IMU) located at a distal tip of the introducer.

9. The steerable-introducer controller of claim 7, wherein the orientation signal defines an angular orientation of a distal tip of the introducer with respect to gravity.

10. The steerable-introducer controller of claim 7, wherein the user reference frame is different from a reference frame of a distal tip of the introducer.

11. The steerable-introducer controller of claim 7, wherein the processor is further programmed to execute instructions for:
    receiving an image from a camera of the introducer; and
    displaying the image on the display screen in the user reference frame.

12. The steerable-introducer controller of claim 11, wherein the steerable-introducer controller is a video laryngoscope including a camera, and the processor is further programmed to execute instructions for:
    receiving an image from the camera of the video laryngoscope; and
    displaying the image from the camera of the video laryngoscope concurrently with the image from the camera of the introducer.

13. The steerable-introducer controller of claim 7, wherein steering the introducer causes a distal tip of the introducer to bend.

14. A steerable-introducer controller, comprising:
    a handle;
    a display screen;
    an introducer port;
    a user input; and a processor within the controller, programmed to execute instructions for:
- receiving, from the user input, a steering command to steer an introducer having a steerable distal tip, the steering command being in a user reference frame;
- receiving, through the introducer port, an orientation signal from an orientation sensor in the distal tip of the introducer;
- translating the steering command as a function of the orientation signal; and
- causing the distal tip to turn according to the translated steering command by controlling a steering wire system at least partially within the introducer.

15. The steerable-introducer controller of claim 14, wherein the orientation signal is from an inertial measurement unit (IMU) located at the distal tip of the introducer.

16. The steerable-introducer controller of claim 14, wherein the orientation signal is from gyroscope located at the distal tip of the introducer.

17. The steerable-introducer controller of claim 14, wherein the user reference frame is different from a reference frame of the distal tip of the introducer.

18. The steerable-introducer controller of claim 14, wherein the processor is further programmed to execute instructions for:
- receiving an image from a camera of the introducer; and
- displaying the image on the display screen in the user reference frame.

19. The steerable-introducer controller of claim 18, wherein the controller is a video laryngoscope.

20. The steerable-introducer controller of claim 19, wherein the processor is further programmed to execute instructions for:
- receiving an image from a camera of the video laryngoscope; and
- displaying the image from the camera of the video laryngoscope concurrently with the image from the camera of the introducer.

* * * * *